United States Patent [19]

Kretz

[11] 4,419,448

[45] Dec. 6, 1983

[54] CONTINUOUS FERMENTATION IN SERIES OF MAIN VESSELS WITH AUXILIARY VESSEL PROVIDED

[75] Inventor: Rolf H. Kretz, Singen, Fed. Rep. of Germany

[73] Assignee: Process Engineering Company SA, Männedorf, Switzerland

[21] Appl. No.: 285,135

[22] Filed: Jul. 20, 1981

[30] Foreign Application Priority Data

Aug. 21, 1980 [CH] Switzerland .................... 6303/80

[51] Int. Cl.$^3$ ............................ C12P 7/06; C12M 1/00
[52] U.S. Cl. ...................................... 435/161; 435/287; 435/813; 435/819
[58] Field of Search ................ 435/161, 287, 302, 800, 435/813, 819; 137/15, 256, 263, 265, 240, 602, 571; 134/18, 22.1, 22.18, 42, 36; 426/29, 30

[56] References Cited

U.S. PATENT DOCUMENTS 3,591,454  7/1971  Laatsch ................................ 435/161
4,238,244  12/1980  Banks ................................ 134/22.18

Primary Examiner—Raymond N. Jones
Assistant Examiner—Elizabeth J. Curtin
Attorney, Agent, or Firm—Michael J. Striker

[57] ABSTRACT

An apparatus for continuously producing alcohol by fermenting a mash containing starch, sugar, and similar carbohydrates includes a series of main fermentation vessels and an auxiliary fermentation vessel. The mash, in mixture with yeast, is transferred in succession through the main vessels during normal operation of the apparatus. When the main fermentation vessels are to be cleaned, the further flow of the mash is diverted into the auxiliary fermentation vessel for a period of time sufficient to empty and clean the first main fermentation vessel in the series, whereupon the supply of the mash to the first main fermentation vessel is restored. The gap in the mash supply propagates through the series of the main fermentation vessels so that the remaining vessels can be in turn cleaned as well. By the time the last of the main fermentation vessels is empty, the mash in the auxiliary fermentation vessel is completely fermented so that it can be used to provide continuity in the stream of fermented product leaving the apparatus. The carbon dioxide developing in the fermentation vessels during the fermentation operation is scrubbed with water and the thus $CO_2$-enriched water is used for washing the inner walls of the fermentation vessels.

10 Claims, 1 Drawing Figure

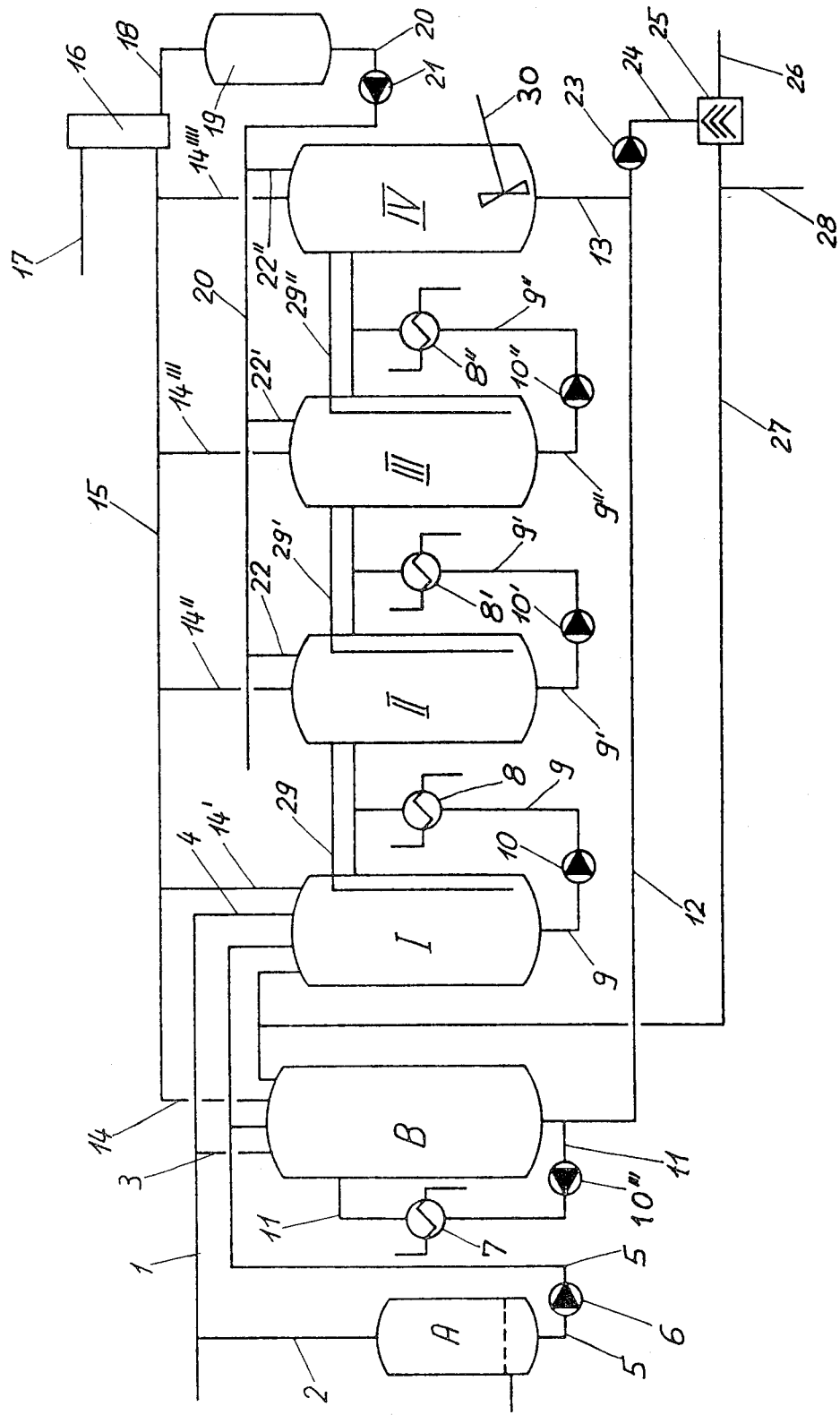

CONTINUOUS FERMENTATION IN SERIES OF MAIN VESSELS WITH AUXILIARY VESSEL PROVIDED

BACKGROUND OF THE INVENTION

The present invention relates to a method and apparatus for producing alcohol by fermentation in general, and more particularly to such a method and apparatus as used in producing the alcohol on a continuous basis.

It is well known that alcohol can be obtained by fermentation of a mash containing starch and/or sugar which constitute nutrients for zymogenic organisms, especially yeasts. In recent years, processes and apparatus have found an ever increasing use in which the fermentation takes place on a continuous basis, rather than in batches, that is, in which the mash is supplied at a steady rate into the apparatus and the fermented mash is withdrawn from a different part of the apparatus at the same rate. Usually, such conventional apparatus includes a plurality of fermentation vessels which are connected in series and between which the mash being fermented is being successively transferred. The continuous production reduces the amount of time spent in the production of alcohol, at least by the amount of time spent in the batch process for filling and emptying the fermentation vessels. However, it has been found that the continuous fermentation cannot be continued indefinitely, particularly since the mash in the vessels eventually becomes "poisoned" by microorganisms which cause chemical reactions different from alcohol fermentation, such as acid fermentation. Therefore, it is necessary from time to time to empty the fermentation vessels and to clean the same, and then to restart the alcohol fermentation process by introducing fresh yeast which does not contain the undesirable microorganisms, or contains only a negligible proportion thereof.

Of course, if it were attempted to clean all the fermentation vessels at the same time, a substantial amount of time would be lost since the cleaning operation would have to await the emptying of the first fermentation vessel in the series, and would last beyond the emptying of the last fermentation vessel in the series, all of which time would be lost as far as the fermentation operation is concerned. During this time, the supply of the mash to be fermented to the apparatus would have to be interrupted, and if the mash were continuously made, as is usually the case, it would have to be accumulated in storage vessels in the interim. Therefore, it is advantageous to maintain a steady flow of the mash into and of the fermented product out of the apparatus, particularly since the accumulation of the mash in the storage vessel brings about at least one significant problem, that is, the contamination of the mash from the ambient atmosphere with the undesirable microorganisms or other contaminants. Obviously, such a contamination results in a loss in the yield of alcohol.

This problem could be at least partially avoided by the provision of an additional fermentation vessel in the series of such vessels, which additional vessel would be put into operation while one or another of the other fermentation vessels is being cleaned. However, under these circumstances, each of the fermentation vessels would have to be capable of serving as the first, second, third, fourth etc. vessel in the series. A continuous alcohol fermentation process and apparatus of this type is known from the published German patent application DE-OS No. 1,642,693, wherein the fermentation vessels of the augmented series can be individually taken out of operation for emptying, cleaning and disinfection by effecting changes in the manner in which the fermentation vessels are interconnected. Thus, the continuous flow of the mash into and of the fermented product out of the apparatus need not be interrupted. While at least theoretically this arrangement is capable of operating in a continuous manner, the piping diagram, the expenditure for the various switching valves, and the operation of the apparatus are so intricate and complex that the total cost is almost prohibitive. Possibly for this reason, arrangements of this type did not find widespread acceptance in the alcohol-producing industry.

SUMMARY OF THE INVENTION

Accordingly, it is a general object of the present invention to avoid the disadvantages of the prior art.

More particularly, it is an object of the invention to provide a continuously operating alcohol fermentation arrangement which is not possessed of the disadvantages of the conventional arrangements of this type.

Still another object of the present invention is to develop an arrangement of the type here under consideration which would render it possible to achieve the cleaning of the individual fermentation vessels in an unproblematical manner and at a low cost in terms of investment and labor.

An additional object of the present invention is to so design the arrangement as to be simple in construction, inexpensive to manufacture and use, and reliable in operation nevertheless.

It is a concomitant object of the invention to devise a method by which the continuous fermentation process and the cleaning of the fermentation vessels could be accomplished not only on a continuous basis as far as the flow of the mash is concerned, but also in a simple and inexpensive way.

In pursuance of these objects and others which will become apparent hereafter, one feature of the present invention resides in a method of producing alcohol by fermentation of a continuously supplied mash containing yeast and yeast nutrients, such as sugar and/or starch, which method, briefly stated, comprises the steps of successively transferring the mash through a series of separate fermentation vessels for fermentation therein during normal operation; and diverting the further supply of mash at intervals and for a predetermined period of time into an intermittently operating auxiliary fermentation vessel for fermentation therein as the mash already present in the series of fermentation vessels continues to be successively transferred through such series during modified operation, especially during cleaning, inspection and/or repair of such fermentation vessels. A particular advantage of this approach is that, by diverting the further mash supply into the auxiliary fermentation vessel, the steady supply of the mash can be maintained, and yet a sufficient amount of the mash will be eventually removed from the fermentation vessels arranged in the series, on a one-by-one basis, to be able to perform the cleaning and similar operations.

Advantageously, the diverting step is continued in each instance at least for a period of time sufficient to empty that of the fermentation vessels of the series which has the longest emptying time. In this manner, it is assured that even this vessel will in turn become empty. It is further advantageous when the period of time during which the mash is being diverted into the auxiliary fermentation vessel exceeds that needed to empty the fermentation vessel in the series having the longest emptying time by an amount sufficient for performing the cleaning operation in this particular vessel following its emptying. In this manner, it is assured that a sufficient amount of time will also be available for cleaning each of the remaining vessels.

According to an advantageous aspect of the present invention, the fermentation of the mash in the auxiliary fermentation vessel is continued until its completion which coincides with the time elapsing between the start of the epmtying of the first fermentation vessel in the series, and the completion of the emptying of the last fermentation vessel in the series. This renders it possible to start the discharge of the fermentation product from the auxiliary fermentation vessel at the same time that the discharge of the fermentation product from the last fermentation vessel in the series terminates, so that continuity can be maintained even at the discharge end of the apparatus.

Following the cleaning operation, the fermentation in the fermentation vessels forming constituent parts of the series is recommended by introducing an enriched fermentation mash from a supply vessel into the first fermentation vessel of the series for about 40 hours, while the fermentation of the mash diverted into the auxiliary fermentation vessel is started and maintained by introducing the enriched mash into the auxiliary fermentation vessel for about 10 hours, following the first introduction of the mash to be fermented into the respective fermentation vessel.

The cleaning, inspection and similar operations are conducted with respect to the individual fermentation vessel in the series as the void or gap in the mash supply in the series of fermentation vessels, which is caused by the diversion of the supply into the auxiliary fermentation vessel, propagates through the fermentation vessels of the series. Advantageously, the cleaning is performed with washing water which has been enriched with carbon dioxide derived from the fermentation vessels.

The apparatus for performing the method of the present invention advantageously includes a plurality of main fermentation vessels; means for transferring the mash through the main fermentation vessels, including conduit means connecting the fermentation vessels in series; an auxiliary fermentation vessel; and means for diverting the mash at intervals and for a predetermined period of time into the auxiliary fermentation vessel, including conduits connecting the auxiliary fermentation vessel with at least some of the main fermentation vessels. Advantageously, the arrangement further includes means for controlling the flow of the mash through the various conduits, including respective valves in such conduits. It is especially advantageous when the auxiliary fermentation vessel has a capacity sufficient to individually accommodate at least the contents of each of the main fermentation vessels.

The novel features which are considered as characteristic of the invention are set forth in particular in the appended claims. The improved fermentation alcohol producing arrangement itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

The sole FIGURE of the drawing is a diagrammatic view of an arrangement according to the present invention.

DETAILED DESCRIPTION OF THE PREFERRED EMBODIMENT

Referring now to the drawing in detail, it may be seen that the reference numeral 1 has been used therein to identify a supply conduit. The supply conduit 1 supplies, on a continuous basis and at a substantially constant supply rate, a sweet mash containing about 14% of fermentable carbohydrates, either to a supply vessel A, a main fermentation vessel I, or an auxiliary fermentation vessel B, depending on the operating circumstances. During normal operation, the conduit 1 supplies the mash to the main vessel I through its extension 4. Then, the mash flows through a conduit 29 into a main fermentation vessel II, from there through a conduit 29' into a main fermentation vessel III, and from there through a conduit 29" into a main fermentation vessel IV. At the same time, the mash is recirculated through an external loop including a respective conduit 9, 9', 9", a recirculating pump 10, 10', 10" respectively, and a heat exchanger 8, 8', 8" to be cooled in the latter.

The main fermentation vessel IV is only provided with a stirring device 30. The fermented mash is withdrawn from the main fermentation vessel IV and is delivered by a pump 23 through a conduit 24 to a yeast separator 25. The yeast separated in the separator 25 in the form of a yeast paste is recirculated in a known manner through a conduit 27 into the main fermentation vessel I.

When it is desired to clean the series of main fermentation vessels I to IV and/or the conduits interconnecting the same, the supply of the mash through the conduit extension 4 is interrupted and the mash is admitted, through a conduit extension 3, into the then empty auxiliary fermentation vessel B. Similarly, the recirculated yeast, if still usable, is admitted from the conduit 27 into the auxiliary fermentation vessel B. The auxiliary fermentation vessel B is so dimensioned that it takes, for instance, 12 hours to fill the same at the steady mash supply rate. Like the continuously operating main fermentation vessels I, II and III, the intermittently operating auxiliary fermentation vessel B is provided with an external cooling system which includes conduits 11, a pump 10''', and a heat exchanger 7.

As soon as the admission of the mash into the main fermentation vessel I is interrupted, the vessel I begins to lose its contents, in that the mash is transferred by the pump 10 through the conduit 9 and the heat exchanger 8 into the main fermentation vessel II, at the same rate at which the mash flows from the vessel I into the vessel II prior to the supply interruption. The main fermentation vessels I, II, III and IV are so dimensioned that each of them accommodates about ten hours worth of flow of the mesh at the steady flow rate. This means that, inasmuch as the fermentation product is continued to be discharged from the main fermentation vessel IV at the steady rate into the conduit 13, the whole series of main fermentation vessels I, II, III and IV would run dry in about 40 hours, that is, all of the vessels I, II, III and IV would be empty by then. However, as mentioned before, the auxiliary vessel B only has a capacity worth 12 hours of flow at the steady supply rate. Since the first main fermentation container I of the series is emptied in about 10 hours, this gives the operating personnel about 2 hours within which to clean the interior of the main fermentation vessel I and/or make minor repairs therein, if necessary. After the expiration of these 2 hours, the auxiliary fermentation vessel B is full and the mash flow to it is discontinued and the mash is again admitted into the now empty and clean first main fermentation vessel I.

At this time, 2 hours worth of mash flow have already been withdrawn from the main fermentation vessel II, so that it takes another 8 hours to completely empty the second main fermentation vessel II in the series. Of course, during this time, no mash is permitted to flow from the vessel I into the vessel II. The emptying of the second main fermentation vessel II takes place through the conduit 9' and the heat exchanger 8', and is accomplished by the pump 10'; the withdrawn mash is admitted into the third main fermentation vessel III of the series. At the time that the vessel II becomes empty, 8 hours worth of flow at the steady rate have been admitted into the first vessel I, and this gives another 2 hours before the vessel I becomes full, which time can be utilized to clean the interior of the vessel II and conduct minor repairs therein. Thereafter, the fresh, partially fermented mash is admitted from the first main fermentation vessel I into the second main fermentation vessel II to gradually fill the same while no mash is being transferred from the vessel II into the vessel III, through the conduit 29. The same operating cycle is then repeated for the following vessels III and IV in the series, under the same conditions.

As mentioned before, the original contents of the fermentation vessels I to IV is completely removed therefrom in about 40 hours, which is the time needed for completing the fermentation either in the main fermentation vessels I to IV, or in the auxiliary fermentation vessel B. This means that, at the close of this 40 hour period, the mash in the auxiliary fermentation vessel B is ready for withdrawal. The mash from the auxiliary fermentation vessel B is then withdrawn through the conduit 12, for instance, at the same rate as mentioned before, so that it would take 12 hours to discharge the contents of the vessel B into the conduit 12, which time period coincides with that which is still needed to completely fill the main fermentation vessels III and IV and complete the fermentation process in the main fermentation vessels I to IV. However, in order to make a sufficient amount of time available for cleaning the yeast separation section, the contents of the auxiliary fermentation vessel can be withdrawn at a more rapid pace, for instance, such that the auxiliary fermentation vessel will become empty in 11 rather than in 12 hours, which gives an extra hour for accomplishing the above task. The excess amounts of mash are in the meantime stored in buffer vessels which are conventional and have not been shown in the drawing, for short periods of time.

A motive for cleaning the continuously operating series of vessels I to IV is given, under usual circumstances, when the contamination of the mash being fermented with foreign microorganisms, which are always present in the incoming mash in minute proportions because it is impossible or would be impractical to handle the incoming mash under sterile conditions, outweighs the beneficial presence of the alcohol-producing yeast in terms of activity. Under these circumstances, it would not make much sense to recirculate the contaminated yeast paste. Thus, the total amount of the yeast is conducted through a conduit 28 to a drying arrangement which is conventional and hence has been omitted from the drawing.

For inoculating the mash with a fresh yeast, the supply fermentation vessel A is so dimensioned as to be able to deliver fresh yeast-enriched mash for 40 to 50 hours. The amount is so selected that it approximately corresponds to the initial concentration in the main fermentation vessel I during the yeast circulation. The supply of fresh mash is accomplished through a conduit extension 2. When it is necessary to inoculate the mash in the fermentation vessels, the yeast suspension is transferred by a pump 6 through a conduit 5 into the fermentation vessels.

The carbon dioxide gas which develops in the fermentation vessels I, II, III, IV and B is fed through a conduit system 14, 15 to a scrubbing device where it is scrubbed with fresh water coming out of a supply conduit 17. The weakly alcoholic carbon dioxide containing washing water is then collected in a buffer vessel 19, after being supplied thereto through a conduit 18, and from there it is pumped by a pump 21 into conduits 20. Additional conduits 22, 22' and 22" lead therefrom to the upper parts of the fermentation vessels where the $CO_2$-enriched washing water is periodically sprayed at the inner surface of the respective vessel upwardly of the liquid level. In this manner, particle deposition at and above the liquid level on the inner surface of the vessel is avoided.

It will be understood that each of the elements described above, or two or more together, may also find a useful application in other types of arrangements differing from the type described above.

While the invention has been illustrated and described as embodied in a mash-fermenting apparatus, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the claims.

What is claimed as new and desired to be protected by Letters Patent is set forth in the appended claims:

1. A method of producing alcohol by fermentation of a continuously supplied mash containing yeast and yeast nutrients, comprising the steps of successively transferring the mash through a series of separate fermentation vessels for fermentation therein during normal operation; diverting the further supply of mash at intervals and for a predetermined period of time into an intermittently operating auxiliary fermentation vessel for fermentation therein as the mash already present in the series of fermentation vessels continues to be successively transferred through such series during modified operation; and continuing the fermentation of the diverted mash in the auxiliary fermentation vessel until completion.

2. The method as defined in claim 1, wherein said diverting step is continued in each instance at least for a period of time sufficient to empty that of the fermentation vessels of the series which has the longest emptying time.

3. The method as defined in claim 2, wherein said predetermined period of time exceeds said sufficient period of time to the extent sufficient to perform a cleaning operation in the longest emptying time fermentation vessel of the series following the emptying thereof.

4. A method of producing alcohol by fermentation of continuously supplied mash containing yeast and yeast nutrients, comprising the steps of successively transferring the mash through a series of separate fermentation vessels for fermentation therein during normal operation; diverting the further supply of mash at intervals and for a predetermined period of time which is at least sufficient for emptying that of the fermentation vessels of the series which has the longest emptying time into an intermittently operating auxiliary fermentation vessel for fermentation therein as the mash already present in the series of fermentation vessels continues to be successively transferred through such series during modified operation; and continuing the fermentation of the mash in the auxiliary fermentation vessel until completion of the fermentation which coincides with the emptying of the last fermentation vessel of the series.

5. A method of producing alcohol by fermentation of continuously supplied mash containing yeast and yeast nutrients, comprising the steps of successively transferring the mash through a series of separate fermentation vessels for fermentation therein during normal operation; diverting the further supply of mash at intervals and for a predetermined period of time which is at least sufficient for emptying that of the fermentation vessels of the series which has the longest emptying time into an intermittently operating auxiliary fermentation vessel for fermentation therein as the mash already present in the series of fermentation vessels continues to be successively transferred through such series during modified operation; and initiating the fermentation process in the fermentation vessels, including introducing an enriched fermentation mash from a supply vessel into the first fermentation vessel of the series for about 40 hours, and into the auxiliary fermentation vessel for about 10 hours, following the first introduction of the mash to be fermented thereinto.

6. The method as defined in claim 1; and further comprising the step of cleaning the fermentation vessels of the series as the void in the mash supply caused by the diversion into the auxiliary fermentation vessel propagates through the fermentation vessels of the series.

7. The method as defined in claim 6, wherein said cleaning step includes capturing carbon dioxide derived from the fermentation vessels in washing water, and washing the respective fermentation vessel with the carbon dioxide enriched washing water.

8. An arrangement for producing alcohol by fermentation of a continuously supplied mash containing yeast and yeast nutrients, comprising a plurality of main fermentation vessels arranged in series and having equal volumetric capacity; means for transferring the mash into, through and out of said main fermentation vessels, including connecting conduit means connecting said main fermentation vessels in series, supply conduit means leading to the first of said main fermentation vessels in said series, and discharge conduit means leading from the last of said main fermentation vessels in said series; an auxiliary fermentation vessel having a volumetric capacity larger than the volumetric capacity of the main fermentation vessels for allowing the continuous supply of mash during cleaning of the main fermentation vessels, said auxiliary fermentation vessel being arranged parallel to the main fermentation vessels and operating discontinuously; and means for diverting a mash at intervals and for a predetermined period of time into said auxiliary fermentation vessel for fermentation therein until completion, including auxiliary supply conduit means connecting said supply conduit means with said auxiliary fermentation vessel.

9. The arrangement as defined in claim 8; and further comprising means for discharging the fermented mash from said auxiliary fermentation vessel into said discharge conduit means after the completion of the fermentation.

10. The arrangement as defined in claim 8, wherein the volumetric capacity of said auxiliary fermentation vessel is sufficient to accept the amount of flow through said supply conduit means at least for the time period needed to empty that of said main fermentation vessels of said series which has the longest emptying time; and wherein said predetermined period of time at least equals said time period.

* * * * *